US007191095B2

(12) United States Patent
Dries (10) Patent No.: US 7,191,095 B2
(45) Date of Patent: Mar. 13, 2007

(54) METHOD AND SYSTEM FOR RECORDING THE RESULTS OF A PSYCHOLOGICAL TEST

(76) Inventor: Christian Dries, Alarichstrasse 75, 50679 Köln (DE)

( * ) Notice: Subject to any disclaimer, the term of this patent is extended or adjusted under 35 U.S.C. 154(b) by 169 days.

(21) Appl. No.: 10/895,735

(22) Filed: Jul. 21, 2004

(65) Prior Publication Data

US 2005/0197802 A1 Sep. 8, 2005

(30) Foreign Application Priority Data

Mar. 8, 2004 (DE) ............ 10 2004 011 124

(51) Int. Cl.
*G21C 17/00* (2006.01)
(52) U.S. Cl. ............ 702/182; 702/127; 702/182; 434/236; 434/118; 707/3; 707/6; 707/101
(58) Field of Classification Search ............ 702/57, 702/127, 182, 183, 187, 189; 434/236, 118; 707/3, 6, 101
See application file for complete search history.

(56) References Cited

U.S. PATENT DOCUMENTS

| 4,354,844 | A | * | 10/1982 | Ickinger | ............ | 434/237 |
|---|---|---|---|---|---|---|
| 5,204,813 | A | | 4/1993 | Samph et al. | | |
| 5,326,270 | A | * | 7/1994 | Ostby et al. | ............ | 434/362 |
| 5,893,098 | A | | 4/1999 | Peters et al. | | |
| 6,629,846 | B2 | * | 10/2003 | Poreh | ............ | 434/236 |
| 2002/0002482 | A1 | | 1/2002 | Thomas | | |
| 2002/0055870 | A1 | | 5/2002 | Thomas | | |
| 2002/0077888 | A1 | | 6/2002 | Chiang | | |
| 2002/0128892 | A1 | | 9/2002 | Farenden | | |
| 2003/0009346 | A1 | | 1/2003 | Shimizu | | |
| 2003/0191777 | A1 | | 10/2003 | Lumsden et al. | | |

(Continued)

FOREIGN PATENT DOCUMENTS

WO WO 01/50403 A1 7/2001

(Continued)

OTHER PUBLICATIONS

Milosavljevic et al., 'Motor Skills with the Altered Visual Feedback', 1996, IEEE Publication, pp. 2265-2266.*

(Continued)

*Primary Examiner*—Carol S. W. Tsai
*Assistant Examiner*—Elias Desta
(74) *Attorney, Agent, or Firm*—Meyertons Hood Kivlin Kowert & Goetzel, P.C.; Jeffrey C. Hood (57) ABSTRACT

A method and a system for recording the results of a psychological test. In particular it concerns a method and a system for recording the results of a test for personnel assessment by at least one observer. One object of the invention is to provide a method and a system for recording the results of a psychological test, which promotes execution of the test and the significance of the test results. That object is attained in that input fields are produced on a display device of a computer, the observer enters the reports in the input fields, the results are stored in a data memory and the computer automatically performs additional functions of result recording and/or test implementation. The invention further concerns a computer program product and a computer system for carrying out the method.

55 Claims, 5 Drawing Sheets

U.S. PATENT DOCUMENTS

| | | |
|---|---|---|
| 2003/0204440 A1 | 10/2003 | Koller et al. |
| 2005/0131716 A1* | 6/2005 | Hanan et al. .................. 705/1 |
| 2005/0192513 A1* | 9/2005 | Darby et al. ................ 600/558 |
| 2006/0015487 A1* | 1/2006 | Vest .............................. 707/3 |

FOREIGN PATENT DOCUMENTS

| | | |
|---|---|---|
| WO | WO 01/95138 A1 | 12/2001 |
| WO | WO 02/13095 A2 | 2/2002 |
| WO | WO 02/21303 A2 | 3/2002 |
| WO | WO02/41113 | 5/2002 |
| WO | WO 03/009187 A1 | 1/2003 |
| WO | WO04/17177 | 2/2004 |

OTHER PUBLICATIONS

German Search Report, Aktenzeichen: 10 2004 011 124.3.

* cited by examiner

| F. Schmidt | T. Maier | H. Busch | K. Knape | C. Dries |
|---|---|---|---|---|
|  | | | | |

INPUT MASK

| Diversity ||||||
|---|---|---|---|---|---|
| ++ | + | O | O/- | - | -- |
| ☐ | ☒ | ☐ | ☐ | ☐ | ☐ |

| Interpersonal Skills ||||||
|---|---|---|---|---|---|
| ++ | + | O | O/- | - | -- |
| ☐ | ☐ | ☒ | ☐ | ☐ | ☐ |

| Communication Skills ||||||
|---|---|---|---|---|---|
| ++ | + | O | O/- | - | -- |
| ☐ | ☒ | ☐ | ☐ | ☐ | ☐ |

| Goalsetting ||||||
|---|---|---|---|---|---|
| ++ | + | O | O/- | - | -- |
| ☐ | ☒ | ☐ | ☐ | ☐ | ☐ |

| Overall impression ||||||
|---|---|---|---|---|---|
| ++ | + | O | O/- | - | -- |
| ☐ | ☒ | ☐ | ☐ | ☐ | ☐ |

++ = far above average
+ = above average
O/- = rather below average
- = below average
-- = far below average

NOTES

FIG. 4

| F. Schmidt | T. Maier | H. Busch | K. Knape | C. Dries |
|---|---|---|---|---|
|  | | | | |

NOTES

| Note 1: | struktures the interview |
|---|---|
| Note 2: | listens attentively |
| Note 3: | asks many questions<br>→ frequently concluded<br>→ does not wait for answers!!! |

| EVALUATION |
|---|

FIG. 5

METHOD AND SYSTEM FOR RECORDING THE RESULTS OF A PSYCHOLOGICAL TEST

TECHNICAL FIELD

The invention concerns a method and a system for recording the results of a psychological test. In particular it concerns a method and a system for recording the results of a test for personnel assessment by at least one observer.

STATE OF THE ART

Nowadays tests are carried out in the most widely varying sectors, for assessment of the emotional and intellectual capabilities of people. Particular commercial significance is attributed to psychological tests of that kind in terms of the assessment of various applications for a post in a corporation, that is to say in terms of personnel assessment. Assessing applicants for posts in large corporations and in particular for management positions is nowadays increasingly performed in establishments which are internationally referred to "assessment centers". An assessment center serves for assessing and evaluating the capabilities and competences of individual applicants on the basis of acknowledged, proven psychological tests. Assessment centers are generally divided into a number of areas in which different tests are carried out. Such tests are for example role playing, plan games, group discussions, individual presentations, case studies and psychological test procedures. In that respect the candidates are observed in situations (practice exercises) which are intended to reproduce as well as possible the demands of the future job. A number of observers record the behavior of the participants in each situation by means of observation sheets. Various capabilities and qualities of each participant are assessed by the observers. The various requirements involved are evaluated on a scale, which permits the various participants to be compared to each other. The scaling further permits to observe differences in performance of individual candidates in various practice situations.

For this purpose the observers generally make use of prepared observation sheets on which assessments and observations are entered in manuscript. The recorded data are brought together in the context of what is referred to as an observer conference and assembled to afford a definitive evaluation of the applicant.

While computer-aided tests have proven their worth for recording the intellectual capabilities and the level of education of the applicants, for example for recording knowledge of mathematics, knowledge of natural sciences or knowledge of languages, in practice no automated methods have proven to be so powerful and informative in regard to the assessment of the characteristic qualities and psychological competitiveness of the applicants, as assessment of the behavior of applicants by trained observers in practice situations. Automatic methods of standardizing and comparing the data relating to individual applicants are also known, without in that respect addressing the procedure of obtaining information, that is to say recording of the test results by at least one observer.

Thus for example US 2002/0055870 describes a method and an apparatus for the comparison of personnel evaluations with evaluation requirements. The procedure involved in acquiring data, in particular personnel assessment, by psychologically trained observers, is here scarcely addressed. The procedure is substantially based on the data which the applicant himself provides about himself.

A fully automatic inquiry system and method is to be found in WO 02/21303. This method may permit automatic processing of the results of interviews conducted by way of a computer and thus rapid evaluation of a large number of inquiry results. In contrast the informativeness and reliability of individual questioning procedures and tests by psychologically trained observers is not achieved here. A similar consideration applies to the apparatus of WO 02/13095. Here, associated with automatic answer recording are automatic prediction means which are intended to ascertain the suitability of individual applicants for a post.

WO 03/009187 describes an Internet-based personnel assessment system. Here, requirement profiles of the employers and test results from the personnel consultants are brought together by way of the Internet. The applicants also have access to that system. This document describes in detail the production of requirement profiles and comparison thereof with evaluation profiles in order as a result to establish a conformity therebetween. The question of recording the performances and evaluation profiles of the applicants is less thoroughly considered. It is proposed that for example technical scientific knowledge is recorded by an online test. The document also refers to the consideration that some areas of competence of the applicant must be recorded at a personal conversation referred to therein as an interview. The results of this interview, after the end of the interview, are entered in a profile which is stored on a computer, of the applicant. The document does not deal with the question of how the evaluation profiles are recorded during an interview by a psychologically trained personnel consultant.

DISCLOSURE OF THE INVENTION

One object of the invention is to provide a method and a system for recording the results of a psychological test, which promotes execution of the test and the significance of the test results.

That object is attained by a method having all of the features of the presently described methods.

As a departure from the usual practice of recording in manuscript the test results noted by the observer, the operation of recording the results is implemented by using a computer, on the display of which are produced input fields in which the results can be entered to be stored in a data memory. That already considerably increases the availability of the results. Thus, an overseer or supervisor can already get to know the impression of the observer or observers while the test is being conducted, by looking at the stored results. In addition the computer automatically executes functions of result recording and/or test implementation.

In a first practical embodiment the computer records the running time of the test, that is to say the time which has elapsed since the beginning of the test. By virtue of this time recording operation, together with an entry in an input field, the test time which has expired at the moment of the entry can be stored by means of the computer. The time of the test which is associated with an entry provides a high level of information both about the applicant and also about the observer. Qualities which the observer enters at an early time appear obvious to the observer. Thus self-confidence and competent appearance of an applicant which are recognized at an early time may have a different importance with respect to certain employment prerequisites than the same self-confidence and competence which is noticed only in the course of a longer interview. The value of an entry can therefore be weighted with the automatically recorded time value.

It will be noted that entries at an inopportune time can also give information about premature or defective assessment. Certain qualities and attributes of a person being tested can be reliably determined only at the end of a given test period. If entries relating to those features are made at an early time, it is possible to deduce therefrom that the observer was rash in arriving at his assessment. In an embodiment of the invention, for results which may be recorded only after a given test time has elapsed, the computer may enable the input fields in question, for receiving an entry, only after a predetermined time.

The result relating to a given criterion, in particular a qualification or a quality of a person being tested, can be recorded in accordance with one embodiment of the invention in the form of a scaled value. A scaled value is generally a value which is between a minimum value and a maximum value. When assessing certain properties of persons being tested, it may be useful for example for evaluations to be recorded in six different steps of far above average (=6) to far below average (=1). In a practical embodiment those results which are recorded in the form of a scaled value, in relation to a given criterion, can be recorded on a plurality of occasions at different times. The sum of all results associated with the specified criterion can be divided by the number of inputs, thereby forming the arithmetic mean of all inputs. That procedure, in relation to a given criterion, not only records the result which is established towards the end of the test by the observer. In relation to that criterion, results are also recorded at the beginning of the test and during the course of the test. That result recordal which is distributed over the course of the test counteracts an effect which occurs when recording only the final result. If it is only the final result that is recorded, then it is generally the last impression gained by the observer that predominates. Recording the result during the course of the test means that the impressions of the observer at the beginning of the test and in the middle of the test are also sufficiently taken into account. In addition the number of entries in relation to a given criterion can allow conclusions to be drawn as to the strength of the impression of an observer, in relation to that given criterion.

In practice the results which are inputted in relation to each given criterion can be stored together with the moment in time of the input thereof. That makes it possible on the one hand to associate a given assessment with given moments in the test. In addition, assessment of the behavior of the observer is also made possible. On the one hand, the entries and the times of the entries of various observers can be compared. In particular entries which are made almost simultaneously by a number of observers enjoy particular significance. Observers, whose observations differ greatly from those of other observers, can be trained on the basis of those items of information. That is possible in particular when the computerized result recordal procedure is coupled and synchronized with a video recording of the test so that the observers can associate the times of their entries with specific events in the test procedure, which are established on the video recording.

In addition protocols about changes in the entries by the observer can also provide information about the applicant, in particular if specific time values are associated with the respective changes, in the protocols. In particular if a test is assessed by a plurality of observers, comparison of the various automatic test protocols with linked time value recordal makes it possible to ascertain whether the change in a quality is to be attributed to a subjective erroneous assessment on the part of an observer or whether it is to be attributed to a change in the behavior of the applicant or the impression given by the applicant. When a number of observers is involved, the latter may result in an approximately simultaneous change in the entry, in relation to given qualities.

Preferably the test results are recorded by a plurality of observers, the computers thereof being networked together. In addition the computers are preferably networked to a server. The server serves for central data storage. As mentioned above, while the test is being performed, a supervisor can view the data on the server and thus find out the assessments made by the observers at an early time. In that situation the test results are preferably written into a common database.

In practice a result file can be automatically produced on the common database. That result file can either be displayed to the supervisor while the test is being performed or it can be used at the end of the test for the observer conference or for presentation of the test results.

A further additional function which in the case of networking the computer can automatically execute for promoting implementation of the test is the communication function. In that respect, in practice at least one computer sends by way of a data network a message which is received and reproduced by at least one other computer. The observers can communicate with each other through that form of communication, without the test procedure being disturbed by that communication. For example short texts can be inputted into a text field and reproduced on a display field on the screen of the message recipient. The computer which receives and displays the messages does not necessarily have to be associated with an observer. It may also be associated with that person who is conducting an interview or performing a test without appearing as an observer. In particular in that case either the observers or a supervisor who also has a computer connected to the data network can communicate items of information and instructions to the person who is carrying out the test or conducting the interview. That happens without the applicant being able to notice the communication and feeling disturbed thereby. The message does not have to be transmitted in the form of a text message but can also be in any other forms and for example can be a spoken message. In that case, a microphone can be connected to the computer of a message sender, and a headset can be connected to the computer of the message recipient, by way of which headset the message transmitted by way of the data network is reproduced without the applicant hearing that.

In practice the inputs into the computer are preferably inputted by way of a touch-sensitive screen, referred to as a touch screen. In particular a Tablet PC is suitable as the computer for the observer. This involves portable computers which have the usual hardware components of conventional notebooks (processor, working memory, hard disk drives, data interface, screen), in which the screen is a touch screen by way of which data inputs can be effected. Tablet PCs are known both in the form of so-called convertibles which can be converted from a conventional notebook by rotating the screen into a Tablet PC with the touch-sensitive screen surface facing upwardly. The casing portion with the keyboard then lies beneath the portion with the screen. A pure Tablet PC does not have a keyboard and only has the casing in which the screen and the other hardware components of the computer are disposed.

The inputs can be effected in different ways on the touch-sensitive screen. For certain qualities, only a limited number of values (for example five different values) may be permissible. In that case an input window may be represented, listing the five values, on the screen of the computer, the selected value being marked and inputted by the observer. A text input can be effected by way of a keyboard. As typing on a conventional keyboard is generally loud and can interfere with the test, it is possible to produce the image of a keyboard on the touch-sensitive screen, with the individual letters being activated by tapping on the images of the respective letters.

In a practical embodiment the inputs are effected in manuscript by way of a touch-sensitive screen. Modem Tablet PCs are equipped with powerful handwriting recognition programs. In the case of reproducible handwriting, the handwriting recognition program can convert the manuscript input into an alphanumeric text and store it as a text file. An image of the manuscript input can additionally or alternatively be stored as an image file. Combined storage of the two different files permits fast automatic further processing of the text file and checking of correct handwriting recognition with the assistance of the image file. A further advantage is that notes stored in the form of a text file can be immediately incorporated into an opinion which is produced on the basis of the test results. In another embodiment a speech recognition program may be executed on the computer to recognize spoken observations or evaluations of the observer. In practice the computer of an observer can produce a plurality of input masks for a plurality of persons who are observed simultaneously during a test. Each of the input masks can be activated by the observer by input with an input means, preferably by touching the touch screen at a given location with an input stylus.

Each of the input masks preferably shows the name of a given person with whom it is associated, in an identification field. The corresponding input mask can be activated by touching that identification field. Additionally or alternatively it is possible for each of the input masks to display a picture of the person with whom it is associated. Displaying the picture of the person makes it possible to avoid an observer entering results relating to a person in the wrong input mask.

For each input mask, the computer can automatically record the total time for which that input mask is activated by the observer during a test. In that way it is possible to establish how intensively an observer was occupied with a given person. The recorded amount of the total time for which the input mask of a given person was activated by the observer can be used to weight the inputs of that observer in relation to that given person.

In practice moreover at least one video recording of implementation of the test can be made. In that way it is possible for observers who are remote from the location of the test to be integrated into implementation of the test. The video recording of the test can be transmitted by way of the Internet or by way of other transmission paths (television satellites and so forth) to a receiving person at any locations in the world, who watches the recording on a screen. That observer, like the observers on site, can enter the results in input fields of his computer. The fact of bringing the entered results together into a central result file by way of the Internet means that the results which are produced at a remote location can be taken into account precisely like the results produced on site. All results are available immediately after the termination of a test.

Alternatively a video recording can be played back with a time shift and an observer can thus produce the results in time-shifted relationship. In that case, the results are available only when the last observer has produced the results, when viewing the video recording.

However the video recording of a test also affords a further advantage in terms of test evaluation, evaluation of the observers and presentation of the test results. Upon test evaluation at an observer conference, an overall assessment can be produced not just on the basis of the times when entries were made, as recorded by the computer, and the recorded results. Those times and the results can also be associated with specific situations during the course of the test. At the same time that permits an assessment of the performance of the observers so that the method can also be used to advantage for assessing observation in the context of education or training.

Finally, in regard to presentation of the test results before a personnel manager who was not personally present at the test, the video recording permits the test results to be clearly set forth by presentation of the actual test procedure by means of the video recording.

In addition one embodiment of the invention concerns a computer program product which for recording the results of a psychological test can be loaded directly into the working memory of a computer and has program code portions which, when the program is executed, perform the steps of the above-described method. The computer program product produces on the one hand the input fields on the display of the computer and receives the entries of the observer and stores them in the data memory. In addition the computer program product contains the required program code portions for executing the automatic functions of result recordal and/or test implementation.

One embodiment of the invention further covers a computer system for recording the results of a psychological test, in particular a test for personnel assessment, by at least one observer, which for each observer includes a computer on which a computer program product as mentioned runs. In practice said computer can include a timer, also referred to as a clock, for automatic time recordal. As mentioned the computer preferably has a touch-sensitive screen. Finally the computer should have a module for wireless data transmission. Networking of the computers of various observers with each other and optionally with a server can in practice be effected by a so-called wireless data network (WLAN=wireless local area network). Such a wireless data network permits data exchange between a wireless access point and a computer over 30 meters and more. The individual observers are therefore not restricted by the networked computer assigned to them in terms of their mobility.

The architecture of the network can be of any nature. In practice the use of a local server which is connected to a wireless access point has proven useful for the network. In operation of larger assessment centers in which different tests are carried out in different rooms the local server can also be connected to a plurality of wireless access points by way of suitable networking so as to ensure reliable data transmission in all rooms of the assessment center.

In practice the local server can be connected to a central server by way of a data network, in particular the Internet. That network architecture has a number of advantages. Professional personnel advisers of large corporations or independent corporations who are specialized in personnel consultation can store on their own server information and files which are required for performing various psychological tests. The fact that a mobile server always has access to the central server by way of a data network guarantees that all assessment centers which are operated by employees of that enterprise access the same up-to-date database. In addition the test results can be communicated from the mobile server to the central server almost in real time. That prevents data loss, for example due to damage to the mobile server, in particular if the central server has reliable data safeguard mechanisms, for example mirroring of a hard disk.

The invention results in a considerable improvement in the level of reliability of assessment recording by human observers. This specification has already described hereinbefore how protocolling of the performance of the observer allows substantial conclusions to be drawn about the quality of evaluation of that observer. In addition the use of computers avoids the transfer of the entries of the respective observers into files which can be processed and stored on computers. That avoids transfer errors. In addition the costs for the work involved in data transfer are eliminated. Finally the data from all observers are available in a database immediately after the termination of the test. That is of crucial significance, in particular for an observer conference which is frequently carried out following a test. Besides the actual inputs from the observers, data analysis can be effected immediately after the test is concluded. For example, conformities on the part of the assessments of various observers can be ascertained. Very high or very low conformities can be automatically marked in a file or in a data display so that they attract attention and can be further discussed at an observer conference.

In addition the evaluation methodology which is presently used can be improved. Hitherto assessments were furnished by the observers in each case once towards the end of the test. Computerized assessment recordal permits a plurality of entries at different times in relation to one assessment criterion so that possibly different impressions at the different moments in time can be protocolled and can be incorporated into the overall assessment. That counteracts the previously known effect where the result is falsified by the last impression. If an applicant makes a very good impression at the end of the test, there is the danger that the assessment turns out to be too good. Conversely, the risk of an excessively poor judgment arises in a situation involving a poor final impression. That result falsification effect can be counteracted by virtue of recording the assessment of individual criteria not just once at the end of the test but a plurality of times during the test. In a practical embodiment a mean value is formed from the results which are entered over the entire time of the test for a given criterion.

Finally it is possible for the data recorded by the method described herein to be transferred into personnel databases, also referred to as human resource databases, which are usually managed by the personnel departments of relatively large corporations.

BRIEF DESCRIPTION OF THE DRAWINGS

Practical embodiments of the system according to the invention for carrying out the method according to the invention are described hereinafter with reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

EMBODIMENTS OF THE INVENTION

Figure 1:
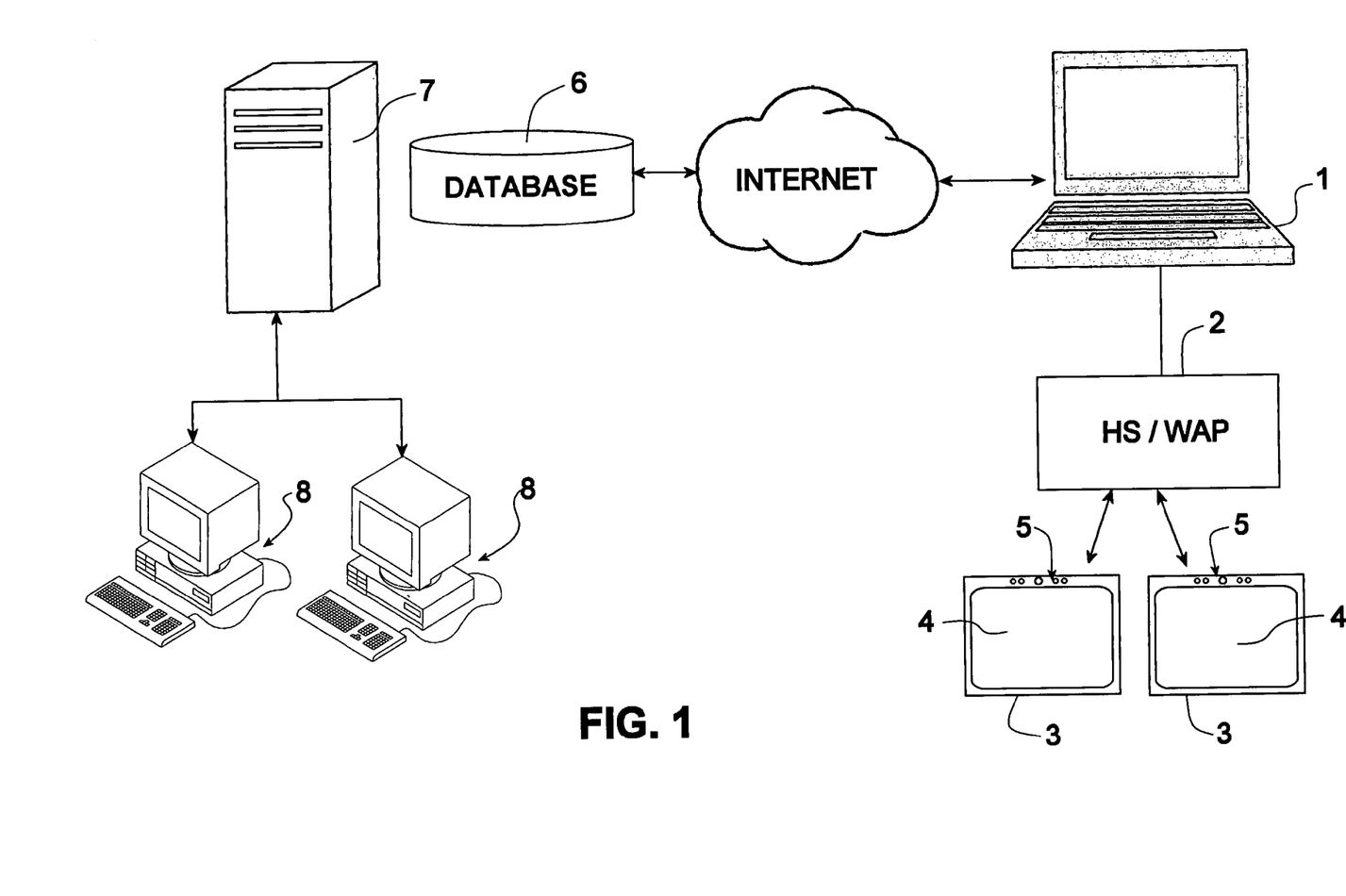
FIG. 1 is a diagrammatic view of a computer system for carrying out the method according to one embodiment of the invention.

FIG. 1 diagrammatically shows the arrangement of a computer system on which the method according to one embodiment of the invention for digitally recording personnel assessment can be carried out. The network for carrying out digital result recordal itself is shown in the right-hand part in FIG. 1. The network comprises a mobile server 1 which in the present case is shown in the form of a notebook computer. The mobile server 1 is configured to communicate in a wireless fashion with a wireless access point 2, also referred to as a hot spot. The wireless access point (WAP) is a network node for a wireless local area network (WLAN). Tablet PCs 3 can exchange data with the mobile server 1 and with each other by way of the wireless access point 2. The Tablet PCs 3 are for that purpose provided with a commercially available WLAN card, that is to say a wireless network access card, which communicates with the access point 2 by way of a common standard for wireless data networks, for example IEEE 802.11g Wireless Standard. In addition a Tablet PC 3 has a touch-sensitive screen 4, referred to also as a touch screen. The touch screen is generally a back-lit LCD flat screen with a touch-sensitive surface. It is however also possible to use other screen technologies which can be integrated in a light mobile device.

Further operating elements 5 of the Tablet PC 3 are mounted to the frame surrounding the screen 4.

The Tablet PC 3 has the usual devices of a mobile personal computer (processor=CPU, working memory=RAM, graphic card, hard disk drive, chargeable battery for power supply and so forth). By virtue of the fact that the Tablet PC 3 communicates with the server 1 by way of a radio network, it does not impede the observer using the Tablet PC 3, in terms of his freedom of movement. Each observer has his own Tablet PC 3 which communicates with the wireless access point (hot spot) 2 by way of the communication of its WLAN card and is thereby networked both with the server 1 and also with the other Tablet PCs 3 of other observers.

The mobile server 1 itself is preferably connected by way of the Internet to a database 6 on a central server 7. The central server 7 can be associated for example with a personnel consultation enterprise or the personnel department of a large corporation. The database 6 of the central server 7 includes all data relevant for the various personnel tests of the corporation in question, in particular prepared input masks which are displayed on the Tablet PCs during recording of the test results and include input fields in which the observer can enter the results. Results of earlier tests can also be stored in the database of the central server 7. The central server 7 is connected by way of its own local area data network to a plurality of workstation computers 8. At the workstations 8 employees of the enterprise can call up, process and store the data on the central server 7.

Finally FIG. 1 shows a video camera 10 connected to a video recording carrier 11 on which video recordings of the test are stored. Preferably digital video recordings are produced, which are stored with a time signal. In that way it is possible for the moment in time in the test to be associated with the moments in time of given entries, which are recorded by way of the Tablet PCs. The recording carrier 11 used can be for example a magnetic tape cassette or preferably a hard disk with a large storage capacity.

The video recording also makes it possible for at least one observer to assess the tested person in time-shifted relationship, in this case also the test time being recorded automatically. Then the beginning of playback of the video recording is assumed to apply as the time of the test start so that the moments in time of the entries made can be associated with the moments in time of the entries actually made during the test by other observers. The time signal of the digital video recording also allows reproduction of the entries of the observers jointly with the playback of the video recording, with the times of the entries being associated with the times of the video recording. It is possible for example at the edge of a video image of the video recording to produce image segments which are associated with given observers and which display the entries thereof in an input mask while the test was being conducted. In that way it is possible not only to check the entries by reference to the video recordings, but it is also possible to check the performances of the observers and possibly improve them in the context of training.

In the system shown in FIG. 1 the digital video recording is transmitted to the database 6 of the server 7 by way of the Internet. If required it can also be called up by way of the mobile server 1. With broadband access to the Internet the data of a digital video signal can be transmitted almost in real time. Only one video camera 10 is shown in FIG. 1. It will be appreciated that a plurality of video cameras 10 can be operated simultaneously and thus different perspectives of the test or different test rooms can be recorded.

Figure 2:
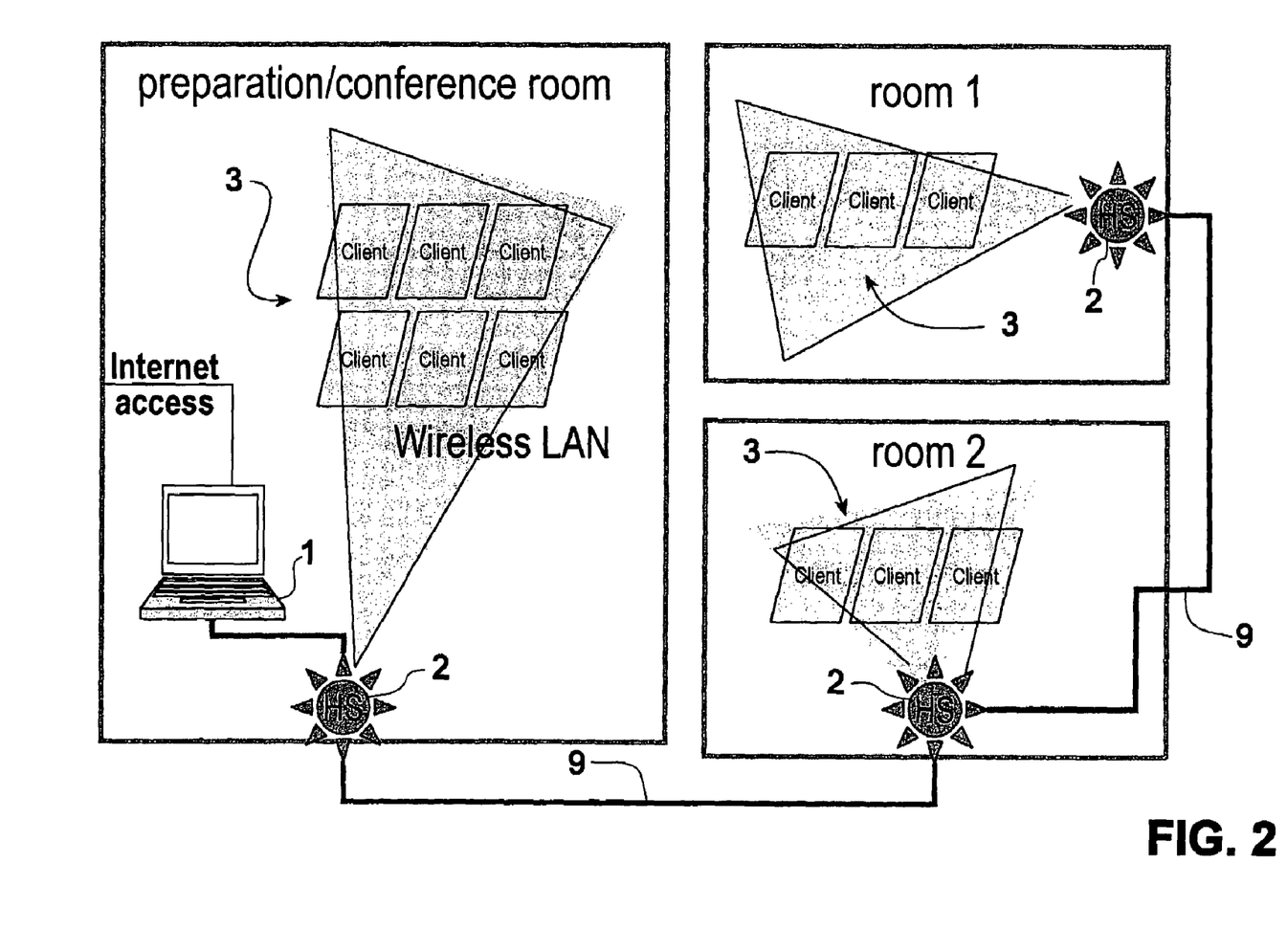
FIG. 2 is a diagrammatic view of the network configuration of the system according to one embodiment of the invention in the rooms of an assessment center.

FIG. 2 shows networking of the individual computers of the system according to one embodiment of the invention for operation of an assessment center. The mobile server 1 is set up in a preparation room or conference room. It is preferably connected to the Internet by way of an Internet access so that it can access data in the central server 7 (see FIG. 1). A hot spot 2, also referred to as a wireless access point, is connected to the mobile server 1. Two further hot spots 2 in different rooms are connected to the hot spot 2 in the conference room by way of data lines 9. Any cable which is suitable for data transfer can be used as a data line 9. Conventional network cables are nowadays in the form of coaxial cables or twisted pair cables. It is however also possible to make a data connection by way of power lines of the power mains of a building. Finally it is also possible to set up radio connections between the various hot spots 2 of the network.

Care is to be taken to ensure that all regions of the rooms of an assessment center in which observers are possibly present are covered by at least one of the hot spots 2 for implementing data transfer. The various hot spots 2 communicate with the WLAN cards in the Tablet PCs 3 on which a client program of the program running on the server 1 runs. The program running on the server 1 is referred in this application as the "digital assessment center".

Figure 3:
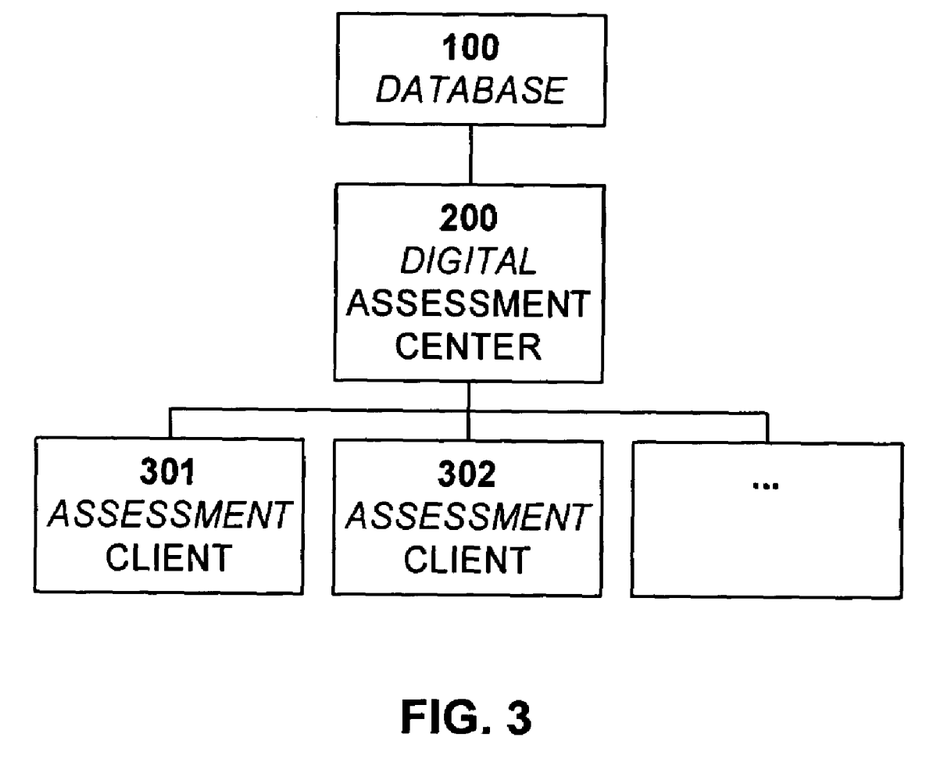
FIG. 3 shows the various program modules which cooperate to carry one embodiment of the invention into effect.

FIG. 3 shows the various program modules which are used for carrying out personnel assessment according to one embodiment of the invention.

It comprises on the one hand a database 100 which is stored on the mobile server 1 (see FIGS. 1 and 2). The database 100 can contain the same items of information as the database 6 (FIG. 1) on the central server 7 of the corporation. It may however also differ from that central database 6 as a connection to the central database is admittedly useful but is not absolutely required, for carrying out the method according to one embodiment of the invention. In this case, the data in the database 100 of the mobile server 1 is preferably co-ordinated from time to time with the data in the database 6 of the central server 7. The data recording program 200 which is identified as the "digital assessment center" runs on the mobile server 1 (FIGS. 1 and 2). An assessment client 301, 302, . . . , runs on each Tablet PC 3 of an observer, that is to say a program which controls result recording on the Tablet PC 3 (FIGS. 1 and 2) and forwards the recorded data to the "digital assessment center" 200 on the mobile server 1.

The "digital assessment center" on the mobile server 1 takes over central control of the result recording programs 301, 302 . . . . It establishes in particular the beginning and the end of the test and, as mentioned, stores the various data which are communicated by the assessment clients 301, 302 . . . . Time recordal can be effected both centrally in the digital assessment center 200 and also decentrally in the individual assessment clients 301, 302 . . . . Decentral time recordal has the advantage that the assessment client 301, 302 . . . is operational even if a short-term interruption occurs in the wireless network connection to the mobile server 1.

On the display device, namely the touch-sensitive screen of each Tablet PC 3, each assessment client 301, 302 produces the masks with the input fields required for result recording.

Figure 4:
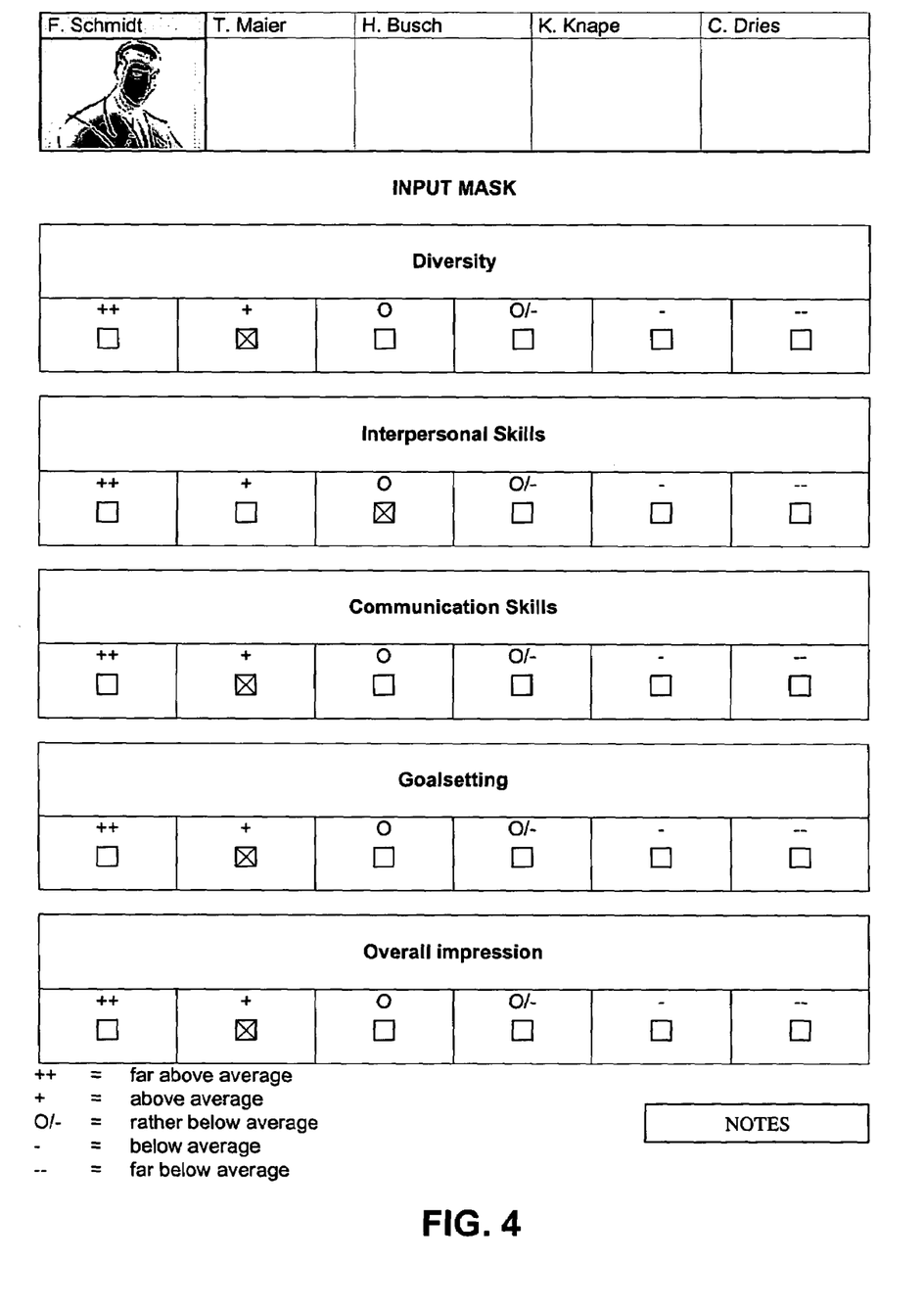
FIG. 4 shows a first example of an input mask for recording the test results.
Figure 5:
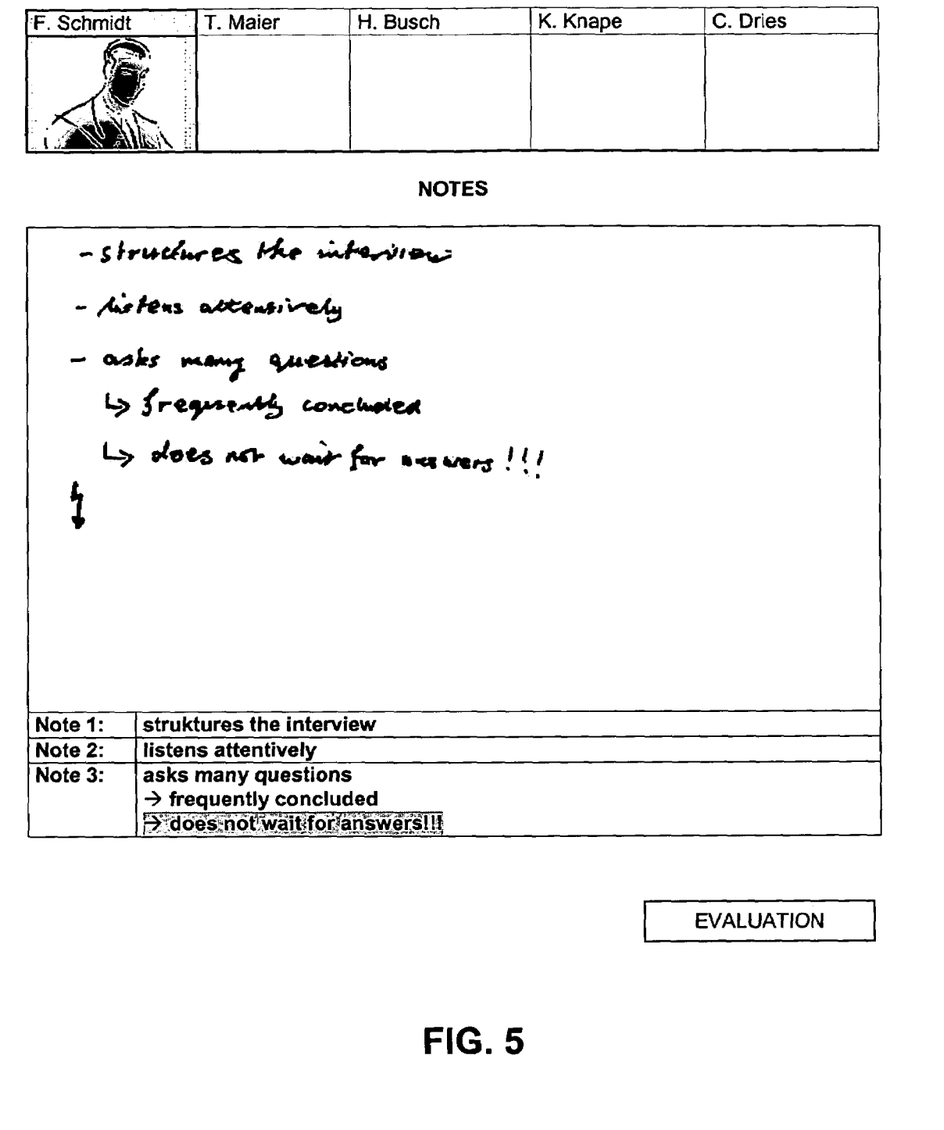
FIG. 5 shows a second example of an input mask for recording the test results.

FIGS. 4 and 5 show examples of such input masks. In this respect the input masks can be activated alternately by so-called flags or tabs at the upper edge of the image, if the procedure is to switch to and for between them. Each input mask is associated with a given person who is participating in the test. The name of the respective person is entered on the flag of the input mask. In addition the input mask can have a field in which a picture of the person is represented. That avoids results from the observers being associated with the wrong person. In FIGS. 4 and 5 the flag of the person F. Schmidt is activated in the left-hand column so that at the same time the picture of Mr. Schmidt is shown. The input mask in FIG. 4 permits the input of five different assessment stages which range from "far above average" to "far below average" and are associated with five different qualities of an applicant, which are to be evaluated by the observer. The evaluation stages associated with the various qualities can be activated by so-called control boxes arranged below the symbols associated with the evaluation stages. Such a procedure makes it possible to achieve comparable assessments by different observers.

In accordance with one embodiment of the invention the Tablet PC 3 which is used as the computer for result recording records not only the evaluation stage selected for each quality but also the moment in time at which the evaluation stage was selected by the observer. In addition the assessment client 301, 302 . . . running on the Tablet PC 3 can also record changes in the evaluation stages in relation to given qualities and store the moments in time associated with the changes. It is possible in that way to arrive at conclusions in regard to changes in the impressions of the observers in the course of a given test.

The program can also be designed in such a way that several results are admitted in relation to a given quality. In that case the evaluation stages which are determined at different moments in time can be entered by the observer in relation to that quality. In practice the mean value of all inputs in relation to a given quality is formed. That ensures that the impressions of a person on the observer are recorded and taken into consideration throughout the entire period of the test. Together with the inputted evaluation stages, the moments in time of the respective input can be recorded by the computer.

Frequently the test results in the form of evaluation stages in relation to given qualities provide too little information about a given applicant. For that reason the assessment client 301, 302 . . . running on the Tablet PC 3, by virtue of the alternative input mask shown in FIG. 5, affords the possibility of manuscript input of notes. That input mask is activated by an observer by touching the function field shown at bottom left and identified by the name "NOTES" on the input mask in FIG. 4 with an input stylus. Equally, by touching the function field with the name "EVALUATION" in the input mask in FIG. 5, the observer can change back to the input mask of FIG. 4. The masks are switched over between the various persons being observed by touching the name flag at the upper edge of the input mask. The computer can automatically record when an observer has activated the input mask of each of the persons being observed. It is possible to conclude therefrom the total time for which an observer devoted himself to each of the persons being considered.

The notes are entered by manuscript by way of the touch-sensitive screen 4 of the Tablet PC 3. A handwriting recognition program converts the manuscript entries into alphanumeric characters, preferably ASCII codes. The result of handwriting recognition is shown at the lower edge of the input mask illustrated in FIG. 5. As in many cases handwriting recognition does not yet operate without error, besides the ASCII codes of handwriting recognition digital image data of the manuscript notes can also be stored. That permits a later check of the notes recognized by handwriting recognition.

The input mask shown in FIG. 5 can also be used for the manuscript input of a message. In that case it is to be coupled to further control fields which are to be represented on the screen 4 and which cause the message to be sent to a given computer or a group of computers in the network. Each computer which is connected to the network of the assessment center acquires a unique address and text messages can be sent for example in the manner of an e-mail message from one computer in the network to another. When the message is received the receiving computer produces on its screen a display window on which the message is displayed in such a way that it can be readily read by the observer.

LIST OF REFERENCES 1 mobile server
2 wireless access point
3 Tablet PC, computer
4 touch-sensitive screen, display device
5 operating elements
6 database
7 server
8 workstation
9 data line
10 video camera
11 recording carrier Although the system and method of the present invention have been described in connection with several embodiments, the invention is not intended to be limited to the specific forms set forth herein, but on the contrary, it is intended to cover such alternatives, modifications, and equivalents as may be reasonably included within the spirit and scope of the invention as defined by the appended claims.

The invention claimed is:

1. A computer-implemented method for performing a psychological test of a test subject for personnel assessment comprising:
    displaying input fields on a computer display, wherein each input field represents a test step in the psychological test;
    conducting the psychological test while an observer observes the test subject;
    receiving observer input in the input fields, wherein the observer input is based on the observer's observations of the test subject;
    measuring one or more response time values related to observer input for each input field, respectively;
    storing results of each test step on a memory medium of a computer system, wherein the results comprise observer inputs in the input fields and the one or more response time values related to observer input for the respective input field; and
    displaying at least some of the results of the psychological test on a display device.

2. The method of claim 1, wherein a response time value comprises an event timestamp that is measured relative to the beginning of the psychological test.

3. The method as recited in claim 1, further comprising: forcing a delay between test steps.

4. The method as recited in claim 1, further comprising: forcing a delay during the execution of a test step.

5. The method of claim 1, wherein a time value comprises the duration of an observer input.

6. The method of claim 1, wherein a touch-sensitive display screen is used to capture observer inputs.

7. The method of claim 1, wherein the test subject is an individual person.

8. The method of claim 1, wherein the observer inputs data into an observer input field for executing a test step.

9. The method of claim 1, wherein plurality of identification fields for the test subject include one or more of:
    the name of the test subject;
    an image of the test subject; and
    personal data of the test subject.

10. The method as recited in claim 1, further comprising: conducting the psychological test while a plurality of observers observe the test subject, wherein the computer systems of each observer are clients in a communication network.

11. The method as recited in claim 10, further comprising: recording the results of each test step on a common database server.

12. The method as recited in claim 11, further comprising: automatically generating a result file for a psychological test from the common database server.

13. The method as recited in claim 10, further comprising: transmitting a message from a first observer to a second observer, wherein a first client computer sends a message to a second client computer over the communications network.

14. The method of claim 1, wherein the observer input is provided in the form of handwriting.

15. The method of claim 14, wherein the observer input is stored in an image file format.

16. The method of claim 14, wherein the observer input is converted to digital alphanumeric text characters and stored in a text file format.

17. The method of claim 1, wherein the test subject is a plurality of persons, wherein for each person, a separate observer mask comprising input fields is provided and displayed, wherein the observer may activate each separate observer mask for input.

18. The method as recited in claim 1, further comprising: recording a video of conducting of the psychological test.

19. The method of claim 18, wherein the video recording is displayed while the psychological test is executed.

20. The method of claim 19, wherein a playback of the video recording of an earlier portion of the psychological test is displayed.

21. The method of claim 19, wherein the results of a test step for at least one observer are displayed concurrently with the view of the video recording.

22. The method as recited in claim 1, further comprising: generating a personnel assessment report from results stored for a psychological test.

23. The method of claim 22, wherein the assessment report includes the results of a statistical analysis of response time values related to observer activity respectively for one or more input fields.

24. The method of claim 23, wherein the statistical analysis is performed across a plurality of observer input fields.

25. The method of claim 23, wherein the statistical analysis is performed across a plurality of test subjects.

26. The method of claim 23, wherein the statistical analysis is performed across a plurality of observers.

27. The method of claim 23, wherein the statistical analysis comprises an average value.

28. The method of claim 22, wherein the personnel assessment report is generated from results stored on a common database server.

29. A computer readable medium for performing a psychological test of a test subject for personnel assessment, wherein the computer readable medium comprises program instructions executable to:
  display input fields on a computer display, wherein each input field represents a test step in the psychological test;
  conduct the psychological test while an observer observes the test subject;
  receive observer input in the input fields, wherein the observer input is based on the observer's observations of the test subject;
  measure one or more response time values related to observer input for each input field, respectively; and
  store the results of each test step on a memory medium of a computer system, wherein the results comprise observer inputs in the input fields and the one or more response time values related to observer input for the respective input field;
  analyze the stored results of each test step to generate an evaluation from the psychological test; and
  display at least some of the evaluation from the psychological test on a display device.

30. The computer readable medium of claim 29, wherein a response time value comprises an event timestamp that is measured relative to the beginning of the psychological test.

31. The computer readable medium as recited in claim 29, wherein the program instructions are further executable to: force a delay between test steps.

32. The computer readable medium as recited in claim 29, wherein the program instructions are further executable to: force a delay during the execution of a test step.

33. The computer readable medium of claim 29, wherein a response time value comprises the duration of an observer input.

34. The computer readable medium of claim 29, wherein the observer inputs data into an observer input field for executing a test step.

35. The computer readable medium as recited in claim 29, wherein the program instructions are further executable to:
  conduct the psychological test while a plurality of observers observe the test subject, wherein the computer systems of each observer are clients in a communication network.

36. The computer readable medium as recited in claim 35, further comprising the programming step of:
  recording the results of each test step on a common database server.

37. The computer readable medium of claim 29, wherein the test subject is a plurality of persons, wherein for each person, a separate observer mask is provided and displayed, wherein the observer may activate each separate observer mask for input.

38. The computer readable medium as recited in claim 29, wherein the program instructions are further executable to:
  generate a personnel assessment report from results recorded for a psychological test.

39. The computer readable medium of claim 38, wherein the assessment report comprises a statistical analysis of response time values related to observer activity for specific observer input fields.

40. The computer readable medium of claim 39, wherein the statistical analysis is performed across a plurality of user-observer input fields.

41. The computer readable medium of claim 39, wherein the statistical analysis is performed across a plurality of test subjects.

42. The computer readable medium of claim 39, wherein the statistical analysis is performed across a plurality of users observers.

43. The computer readable medium of claim 39, wherein the statistical analysis comprises an average value.

44. The computer readable medium of claim 38, wherein the personnel assessment report is generated from results stored on a common database server.

45. A system for performing a psychological test of a test subject for personnel assessment comprising:
  a display device;
  a processor; and
  a memory medium coupled to the display device and the processor, wherein the memory medium stores a computer program comprising instructions executable by the processor to:
  display input fields on a computer display, wherein each input field represents a test step in the psychological test;

conduct the psychological test while an observer observes the test subject;

receive observer input in the input fields, wherein the observer input is based on the observer's observations of the test subject; measure one or more response time values related to observer input for each input field, respectively; and store the results of each test step on a memory medium of a computer system, wherein the results comprise observer inputs in the input fields and the one or more response time values related to observer input for the respective input field;

analyze the stored results of each test step to generate an evaluation from the psychological test; and display at least some of the evaluation from the psychological test on a display device.

46. The system of claim 45, wherein a response time value comprises an event timestamp that is measured relative to the beginning of the psychological test.

47. The system as recited in claim 45, wherein the program instructions are further executable to:

force a delay between test steps.

48. The system as recited in claim 45, wherein the program instructions are further executable to:

force a delay during the execution of a test step.

49. The system of claim 45, wherein a time value comprises the duration of an observer input.

50. The system of claim 45, wherein the system is a portable computer system.

51. The system as recited in claim 45, further comprising:

a video camera for recording a video of the psychological test.

52. The system of claim 45, wherein the display device is coupled to a touch-sensitive input device.

53. The system of claim 45, further comprising:

a network interface adapter.

54. The system of claim 53, wherein the network interface adapter is operable for connecting to a wireless network.

55. The system of claim 53, wherein the network interface adapter is operable for connecting to the Internet.

* * * * *

UNITED STATES PATENT AND TRADEMARK OFFICE
CERTIFICATE OF CORRECTION

| | | |
|---|---|---|
| PATENT NO. | : 7,191,095 B2 | Page 1 of 1 |
| APPLICATION NO. | : 10/895735 | |
| DATED | : March 13, 2007 | |
| INVENTOR(S) | : Christian Dries | |

It is certified that error appears in the above-identified patent and that said Letters Patent is hereby corrected as shown below:

Column 12 Lines 52-53, please delete "claim 1, wherein plurality of identification fields for" and substitute -- claim 1, wherein a plurality of identification fields for --;

Column 14 Lines 42-43, please delete "across a plurality of user-observer input" and substitute -- across a plurality of observer input --;

Column 14 Lines 48-49, please delete "across a plurality of users observers." and substitute -- across a plurality of observers. --.

Signed and Sealed this

First Day of May, 2007

JON W. DUDAS
*Director of the United States Patent and Trademark Office*